United States Patent
Klein et al.

(10) Patent No.: US 7,459,575 B2
(45) Date of Patent: Dec. 2, 2008

(54) ALUMINUM TRILACTATE POWDER AND METHOD FOR PREPARATION

(75) Inventors: Cornelis Jan Ir. Klein, Blair, NE (US); Marcus Johannus Anthonius Wilhelmus Vorage, Balloo (NL)

(73) Assignee: Purac Biochem B.V., Gorinchem (NL)

( * ) Notice: Subject to any disclaimer, the term of this patent is extended or adjusted under 35 U.S.C. 154(b) by 0 days.

(21) Appl. No.: 12/000,172

(22) Filed: Dec. 10, 2007

(65) Prior Publication Data

US 2008/0154054 A1 Jun. 26, 2008

Related U.S. Application Data

(60) Provisional application No. 60/874,727, filed on Dec. 14, 2006.

(51) Int. Cl.
*C07F 5/06* (2006.01)
*A61K 8/02* (2006.01)

(52) U.S. Cl. .............. 556/183; 556/185; 424/401; 424/402

(58) Field of Classification Search ............. 556/183, 556/185; 424/401, 402
See application file for complete search history.

(56) References Cited

U.S. PATENT DOCUMENTS 5,274,152 A 12/1993 Carmody

FOREIGN PATENT DOCUMENTS

| JP | A 57-080340 | 5/1982 |
| JP | A 58-067644 | 4/1983 |
| JP | A 61-060631 | 3/1986 |
| JP | A 09-002999 | 1/1997 |

OTHER PUBLICATIONS

Rai, A.K. et al., "Derivatives of Aluminum with Some α-Hydroxy Carboxylic Acids," Journal fur praktischen Chemie 4 (20) p. 105-112 (1963).

*Primary Examiner*—Porfirio Nazario Gonzalez
(74) *Attorney, Agent, or Firm*—Oliff & Berridge, PLC

(57) ABSTRACT

The present invention relates to a spray-drying method for the preparation of a new aluminum trilactate powdery product and to the resulting significantly free-flowing and not significantly sticky nor dusty product itself. The invention is also directed to product applications in which said aluminum lactate product may be applied.

9 Claims, 2 Drawing Sheets

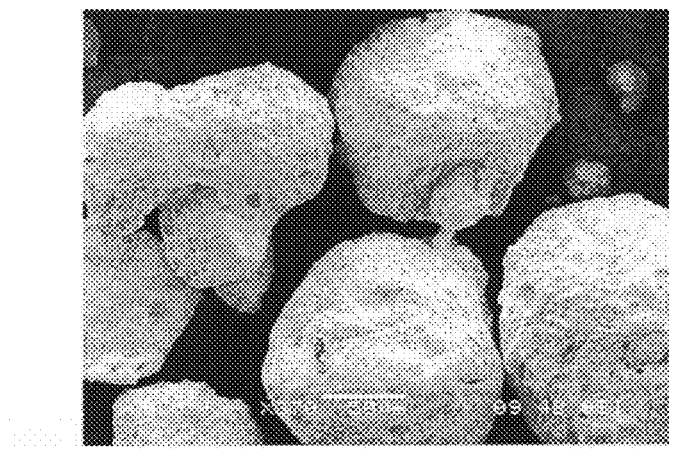
Figure 1: SEM picture obtained via the scanning electron microscope technique of spray-dried aluminum tri-lactate powder according to the present invention.

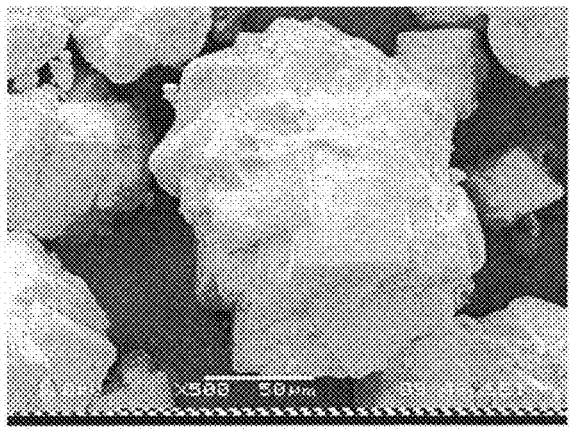
Figure 2: SEM picture of commercially available aluminum tri-lactate powder.

ALUMINUM TRILACTATE POWDER AND METHOD FOR PREPARATION

The present invention relates to a method for the preparation of a new aluminum trilactate powdery product and to the product itself. Further, the invention is directed to product applications in which said aluminum lactate product may be applied.

A method for the preparation of aluminum trilactate powder is described in an article from 1962 by A. K. Rai, R. K. Mehrotra and R. C. Mehrotra (Journal für praktischen Chemie, 4 (20), pages 105-112). This article describes the formation of aluminum trilactate by precipitation due to the reaction of aluminum chloride or aluminum isopropoxide with lactic acid. In both reactions the precipitate is washed with ether and dried at about 60-70° C./1.0 mm·Hg.

More recent prior art, Japanese patent application 61-060631 by Sunahara (1986), describes a production method for aluminum trilactate wherein metallic aluminum reacts directly with a lactic acid solution in presence of a catalyst. The resulting aqueous solution, sometimes containing partly precipitated aluminum lactate, is optionally further concentrated, filtered and dried.

An other Japanese patent application 09-002999 by Yamamoto (1997) mentions the formation of aluminum trilactate by addition of lactic acid to a basic aluminum lactate solution having a lactic acid/aluminum oxide molar ratio of 0.5-5 up to the extent wherein aluminum trilactate is formed, which corresponds with a molar ratio of 5.8-6.2 of lactic acid/aluminum oxide.

The present invention provides a new method for the preparation of aluminum trilactate. The new method has various advantages in comparison to above-mentioned production methods. The new production method is very efficient, has a high product yield, has minimal product losses and low production costs and does not generate waste byproducts in contrast to precipitation/crystallization processes. This latter type of process always generates a byproduct in the form of a "mother liquor" comprising non-crystallized product. This mother liquor remains behind after filtration of the crystallized/precipitated product.

Further, in the new production method according to the present invention no auxiliary materials are needed such as catalysts or washing agents as e.g. ether.

The new production method is not complex and easy to (automatically) control and as a consequence a product of constant quality is achieved.

The present invention further provides a new aluminum trilactate powdery product that is easy to handle and transport unlike the present commercially available aluminum trilactate powder. Commercially available aluminum trilactate powder is relatively dusty and sticky and the flowability is not satisfactory. These unfavorable powder properties often lead to practical and safety problems in handling and transporting the powdery product. Further, the stickiness of the product results in high product losses and low yields. It further requires intensive, time consuming and costly cleaning of the used equipment and pipelines. These problems are overcome with the product of the present invention.

BRIEF DESCRIPTION OF THE DRAWINGS

FIG. 1 is a SEM picture obtained via the scanning electron microscope technique of spray-dried aluminum tri-lactate powder according to the present invention; and FIG. 2 is a SEM picture of commercially available aluminum tri-lactate powder.

The present invention is directed to a method for the preparation of aluminum trilactate comprising a spray drying process wherein a solution comprising aluminum trilactate and/or an aluminum trilactate slurry is atomized and the atomized droplets are contacted with heated gas resulting in the formation of solid aluminum trilactate particles, followed by the separation of the solid particles from the gas. The solution or slurry can comprise between 10 to 70 wt % of aluminum trilactate.

The spray drying process can take place in the various well-known commercially available spray-drying equipment and apparatus in which the heated gas and the aluminum trilactate solution flow co-currently, counter-currently, as a mixed flow in the dryer, etceteras.

The heated gas, for example air at reduced pressure (e.g. vacuum of 0.5 to 5 mbar), is used for the evaporation or the drying of the sprayed droplets. The drying process may be performed in one stage, meaning in one pass through the dryer, or in multiple stages.

The nozzles, through which the solution is pumped and atomized, may be located at the top, at the bottom or sideways in the dryer. Different types of nozzles are possible. In a preferred embodiment of the present invention, the nozzles are located at the top and the heated air is introduced mainly from above to flow co-currently with the spray of droplets.

The atomization may be performed by using rotary atomizers, high pressure nozzles or two-fluid nozzles or combinations hereof. It was found that low concentrated aluminum trilactate solutions (including slurry's) are preferably atomized with two-fluid nozzles and the use of compressed air or steam. The concentrations are in the order of 10-25 wt % of aluminum trilactate.

Higher concentrated aluminum trilactate slurry's, with concentrations of about 25-70 wt % and in particular 40-55 wt % aluminum trilactate may also be atomized with two-fluid nozzles and the use of compressed air or steam but are preferably atomized by means of high pressure.

The aluminum trilactate solution or slurry that is used as feed for the spray drying process may be obtained by various means such as for example by means of reaction or crystallization/precipitation.

In a preferred embodiment of the present invention, the aluminum lactate feed solution is obtained via reaction of an aqueous lactic acid solution with aluminum hydroxide powder in the presence of water in a molar ratio of 3 to 1 (lactic acid:aluminum trihydroxide).

In a preferred embodiment of the present invention, the sprayed droplets are falling down while being dried by the heated air. After this first drying stage the particles may be taken through a second drying stage that may be integrated in the bottom section of the spray tower. Said bottom section then comprises an integrated bed through which heated air flows for further drying of the particles. This drying step may also be performed externally in separate drying equipment.

The particles are after the first and/or second drying step subsequently further transported via a shaking or vibrating bed. This shaking or vibrating bed serves for further conditioning as e.g. cooling down of the particles. The particles then may be taken through a classification system comprising sieves and mills if more fine-tuning of the particle size is required. The fines after milling may be recycled back to the spray section of the spray tower.

The method yields a product that is free-flowing, not significantly dusty or sticky and which comprises nicely almost round shaped or spherical particles in contrast to the commercially available aluminum trilactate products. These latter products comprise particles with many edges looking more like cubical and pyramid shaped blocks or of a form in between. These rod- or cubical-shaped particles are an indication that said particles are made via crystallization processes. The nicely spherical-shaped aluminum trilactate particles of the present invention have a much narrower particle size distribution compared to commercially available aluminum trilactate. Particles sizes between 50 and a 1000 micrometer and more in particular between 100 and 500 or even between 100 and 300 micrometer are easy achievable. The aluminum trilactate powder of the present invention includes these particles up to a 1000 micrometer in particle size. The powder of the present invention has further a very high flowability and is visibly less dusty than commercially available aluminum trilactate powder. The powder has a Hausner ratio (a well-known parameter to express or indicate the degree of flowability with) of below 1.15. This means that it is easier to transport and to handle and the caking tendency is less than with commercially available aluminum trilactate. A Hausner ratio of higher than 1.4 means that the powder is cohesive and thus more difficult or even not suited for proper handling and transport. Further, the new product shows a very high dynamic flow rate of 50 ml/s and higher (e.g. 60-70 ml/s) to even above 80 ml/s which is about twice as high as commercially available aluminum trilactate powder. The same applies for the dissolution rate, which is about a factor two higher for the new product.

Said high dynamic flow rate and dissolution rate are very favorable in handling and transporting the powder. The high dissolution rate makes the powder very suited for various applications.

Due to the advantageous powder properties mentioned above, the aluminum trilactate powder obtained via the present invention was found to be very suitable for various product applications such as cosmetic and personal care applications, dental or oral care applications and technical applications.

The following non-limiting examples illustrate the invention.

EXAMPLE I

A solution was made comprising 20 wt % aluminum trilactate by reaction of a solution comprising 88 wt % of lactic acid with ~80 wt % dried aluminum hydroxide gel (a white amorphous powder product obtained from Taurus Chemicals®) in the presence of demineralized water. The reaction was carried out at an elevated temperature of about 75 to 80° C. and with a molar ratio of 3 to 1 for lactic acid to aluminum hydroxide.

The resulting 20 wt % solution was fed to a spray-dry tower. The solution was fed through two-fluid type nozzles (located at the top of the tower) and atomized by means of application of steam under a pressure of about 8 to 10 bar. The spray of droplets was brought in contact with heated air (mainly introduced from above in the spray dry tower) with an inlet temperature of about 235 to 245° C. The outlet temperature was about 100 to 120° C.

The spray-dried particles were further introduced in a static bed integrated in the lower section of the tower for further drying and were subsequently transported via a shaking bed for cooling down. The particles were then taken through a classification system comprising sieves and a mill.

The result was a free-flowing, non-dusty and non-visually noticeably sticky powder comprising about 97 wt % of aluminum trilactate powder with a 3 wt % moisture content. SEM pictures of the powder composition showed almost completely round or spherical shaped particles (some agglomerated together) in contrast to commercially available aluminum trilactate powder as e.g. PURAMEX AL® of PURAC Biochem B.V as is shown in FIGS. 1 and 2.

A particle size distribution (PSD), measured via a Malvern mastersizer 2000®, showed the following parameters: a d0.1 (micrometer) of about 110, a d0.5 (micrometer) of about 180 and a d0.9 (micrometer) of about 300.

The degree of flowability of the powder is indicated via the well-known Hausner ratio, which was calculated and measured by measurement of the compressed or tapped bulk density and the untapped (uncompressed) aerated bulk density. The values of the parameters are shown in TABLE I. The experiments were done in duplicate.

TABLE I

Bulk density results.

| Sample | Aerated Density (untapped) (g/cc) | Density tapped (g/cc) | Hausner ratio | Carr Class or compressibility % |
|---|---|---|---|---|
| Al - trilactate | 0.621 | 0.669 | 1.08 | 7.2% Excellent |
| Al - trilactate | 0.604 | 0.671 | 1.11 | 10% Excellent |
| Commercial Al-trilactate powder | 0.706 | 0.817 | 1.16 | 13.6% Good |
| Commercial Al-trilactate powder | 0.706 | 0.824 | 1.17 | 14.3% Good |

The "Carr class" is a known index or scale (R.I. Carr, 1965, Evaluation of flow properties of solids) based on compaction and used to compare the flow properties of various powders with each other. The expressions "good" and "excellent" on this scale indicate that the powders of the invention are very well and even excellent free-flowing. It further indicates that in handling and transporting the powders, e.g. packaged in big bags, the powders are not significantly compressed. As a consequence, the big bags are not suddenly "half empty" when they reach the customer.

The flowability can also be expressed by measurement of the dynamic flow rate, which is also a standardized method. The dynamic flow rate is measured by measuring the time for 600 ml of powder product to flow through a 2 cm orifice of a tube. A dynamic flow rate of or above 50 and preferably of or above 70 or 80 ml/s is acceptable in terms of the powder being suited for the normal handling and transporting activities. The higher the dynamic flow rate, the easier and more efficient, in terms of time and losses of powder that remains behind, the handling and transport of the powder will be.

The measured values are shown in TABLE II.

TABLE II

The dynamic flow rate

| Sample | Dynamic flow rate (ml/s) | Class/Scale |
|---|---|---|
| Al - trilactate | 86.1 | Acceptable |
| Al - trilactate | 85.7 | Acceptable |
| Commercial Al-trilactate powder | 45.9 | Bad |
| Commercial Al-trilactate powder | 43.4 | Bad |

The dissolution rate of both powders was measured by measuring the time necessary to dissolve 5 g of aluminum trilactate in 200 ml of Milli-Q water at room temperature. The conductivity of the solution was measured in time. When the conductivity is stable, the sample is considered to have dissolved.

The spray-dried aluminum trilactate powder showed a two-fold higher dissolution rate of about 0.25 g/s (or 20 seconds per 5 grams of powder) compared to PURAMEX AL® with a dissolution rate of about 0.125 g/s (or 40 seconds per 5 grams of powder).

EXAMPLE II

A approximately 53 wt % aluminum lactate-comprising slurry was made by slow and controlled addition of about 16 kg of ~80 wt % dried aluminum hydroxide gel (a white amorphous powder product obtained from Taurus Chemicals®) to about 55.8 kg of lactic acid and about 25.4 kg of demineralized water at an elevated temperature of about 75 to 85 degrees Celsius.

The aluminum trilactate slurry was kept in a feed tank and was continuously stirred. The slurry was fed from the feed tank to a commercially available SLS small-scale pilot spray dryer. The slurry was fed through two-fluid type nozzles (located at the top of the tower) and atomized by means of compressed air. The spray of droplets was brought in contact in co-current flow with heated air with an inlet temperature of about 220 to 230° C. The outlet temperature was about 120 to 130° C.

The resulting free-flowing aluminum trilactate powder had a moisture content of about 1.1 wt %.

The invention claimed is:

1. A method for the preparation of aluminum trilactate powder comprising a spray drying process wherein a solution or slurry comprising aluminum trilactate is atomized to droplets and the droplets are contacted with heated gas resulting in the formation of solid aluminum trilactate particles followed by the separation of the solid particles from the gas.

2. The method according to claim 1 wherein the gas is air at reduced pressure.

3. The method according to claim 1 wherein the solution or slurry is atomized by means of applying compressed air or steam and using a two-fluid nozzle or by means of applying high pressure and a high pressure nozzle.

4. The method according to claim 1 wherein the aluminum trilactate solution or slurry comprises 10-70 wt % of aluminum trilactate.

5. Aluminum trilactate powder obtainable by the method according to claim 1.

6. Aluminum trilactate powder of claim 5 having a Hausner ratio of less than 1.15.

7. Aluminum trilactate powder of claim 5 having a dynamic flow rate of at least 50 ml/s.

8. Aluminum trilactate powder of claim 5 having a dissolution rate of above 0.125 g/s in water at ambient room temperature.

9. A personal care, cosmetic, or dental product comprising the aluminum trilactate powder of claim 5.

* * * * *